United States Patent
Ozeki et al.

(10) Patent No.: US 10,422,701 B2
(45) Date of Patent: Sep. 24, 2019

(54) TEMPERATURE SENSOR

(71) Applicant: DENSO CORPORATION, Kariya, Aichi-pref. (JP)

(72) Inventors: Toshiya Ozeki, Kariya (JP); Koichi Yoshida, Kariya (JP); Motoki Sato, Kariya (JP); Masaki Hironaka, Kariya (JP)

(73) Assignee: DENSO CORPORATION, Kariya (JP)

( * ) Notice: Subject to any disclaimer, the term of this patent is extended or adjusted under 35 U.S.C. 154(b) by 164 days.

(21) Appl. No.: 15/563,706

(22) PCT Filed: Apr. 1, 2016

(86) PCT No.: PCT/JP2016/060887
§ 371 (c)(1),
(2) Date: Oct. 2, 2017

(87) PCT Pub. No.: WO2016/159337
PCT Pub. Date: Oct. 6, 2016

(65) Prior Publication Data
US 2018/0073936 A1    Mar. 15, 2018

(30) Foreign Application Priority Data

Mar. 9, 2016 (JP) ................................. 2016-046037

(51) Int. Cl.
*G01K 1/14* (2006.01)
*G01K 1/08* (2006.01)
(Continued)

(52) U.S. Cl.
CPC ................. *G01K 1/08* (2013.01); *G01K 1/12* (2013.01); *G01K 7/18* (2013.01); *G01K 7/22* (2013.01);
(Continued)

(58) Field of Classification Search
CPC ........................................................ G01K 1/14
See application file for complete search history.

(56) References Cited

U.S. PATENT DOCUMENTS 8,256,956 B2 * 9/2012 Suzuki .................. G01K 13/02
374/163
10,024,726 B2 * 7/2018 Yoshida .................. G01K 1/08
(Continued)

FOREIGN PATENT DOCUMENTS

| JP | 2009-281965 | 12/2009 |
| JP | 2009-294107 | 12/2009 |

(Continued)

*Primary Examiner* — Clayton E. LaBalle
*Assistant Examiner* — Leon W Rhodes, Jr.
(74) *Attorney, Agent, or Firm* — Nixon & Vanderhye P.C.

(57) ABSTRACT

A temperature sensor includes a temperature detector, an element electrode wire, a lead wire, and an intermediate member. Each of the lead wire and the intermediate member is made of a Ni-based alloy or an Fe-based alloy. The element electrode wire and the intermediate member are welded together in such a manner that opposing surfaces, facing each other abut against each other to constitute an element-side weld. The intermediate member and the lead wire are welded together such that they overlap each other in a longitudinal direction Z to constitute a lead-side weld. The lead wire is extended closer to the temperature detector than the element-side weld is located. A gap between the element electrode wire and the lead wire at least in the longitudinal direction Z is filled with a filler. The element electrode wire, the element-side weld, and the lead wire are fixed to one another by the filler.

8 Claims, 8 Drawing Sheets

(51) Int. Cl.
    *G01K 7/22*      (2006.01)
    *G01K 1/12*      (2006.01)
    *G01K 7/18*      (2006.01)
    *G01N 27/406*    (2006.01)
    *G01N 27/407*    (2006.01)

(52) U.S. Cl.
    CPC ..... *G01N 27/4062* (2013.01); *G01N 27/4078* (2013.01); *G01K 2205/04* (2013.01)

(56) References Cited

U.S. PATENT DOCUMENTS

| | | |
|---|---|---|
| 2009/0323765 A1 | 12/2009 | Yokoi et al. |
| 2013/0223479 A1 | 8/2013 | Satou et al. |
| 2014/0092940 A1 | 4/2014 | Suzuki et al. |
| 2017/0138796 A1 | 5/2017 | Yoshida et al. |

FOREIGN PATENT DOCUMENTS

| | | |
|---|---|---|
| JP | 2011-38926 | 2/2011 |
| JP | 2012-52959 | 3/2012 |

\* cited by examiner

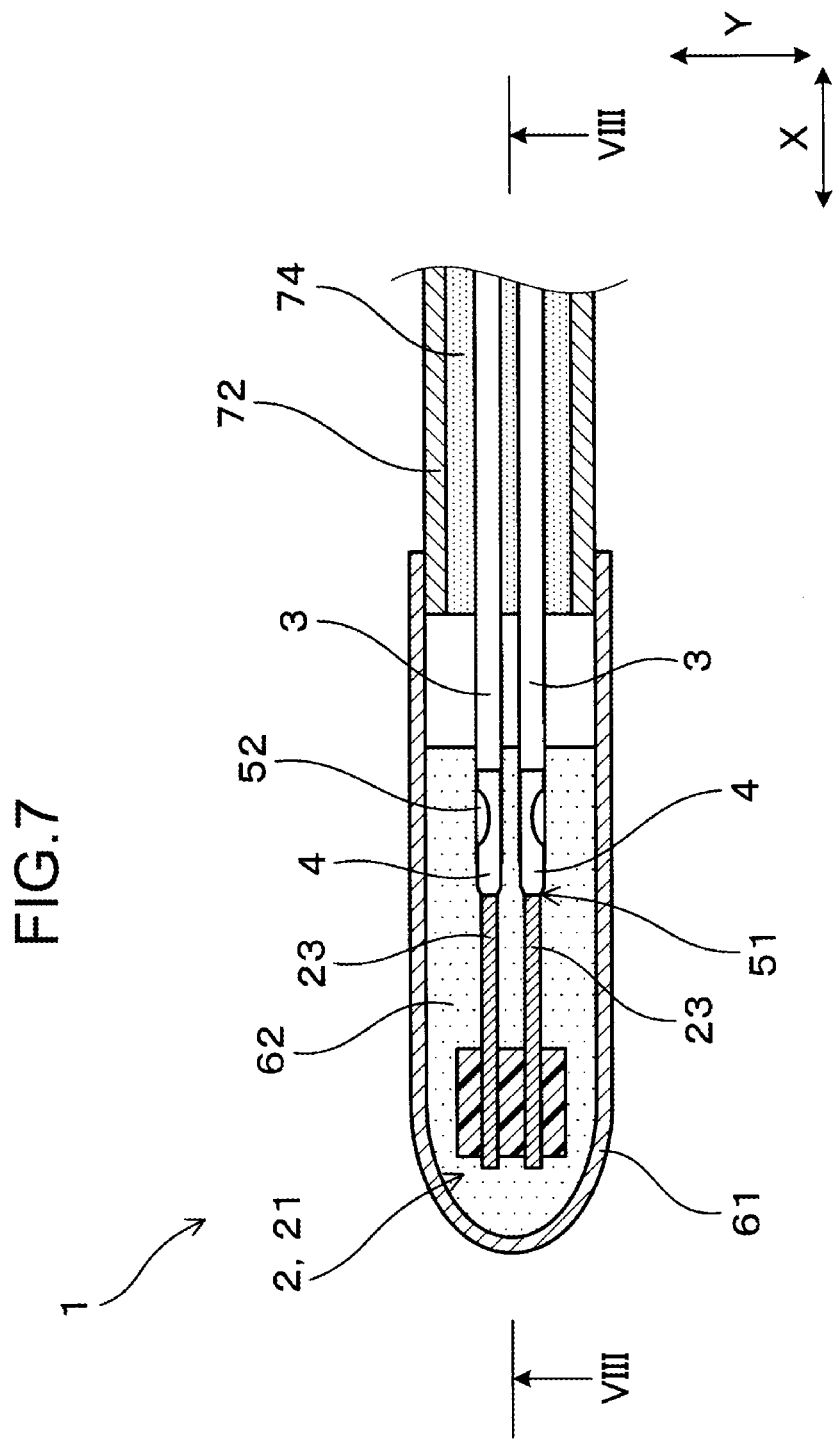

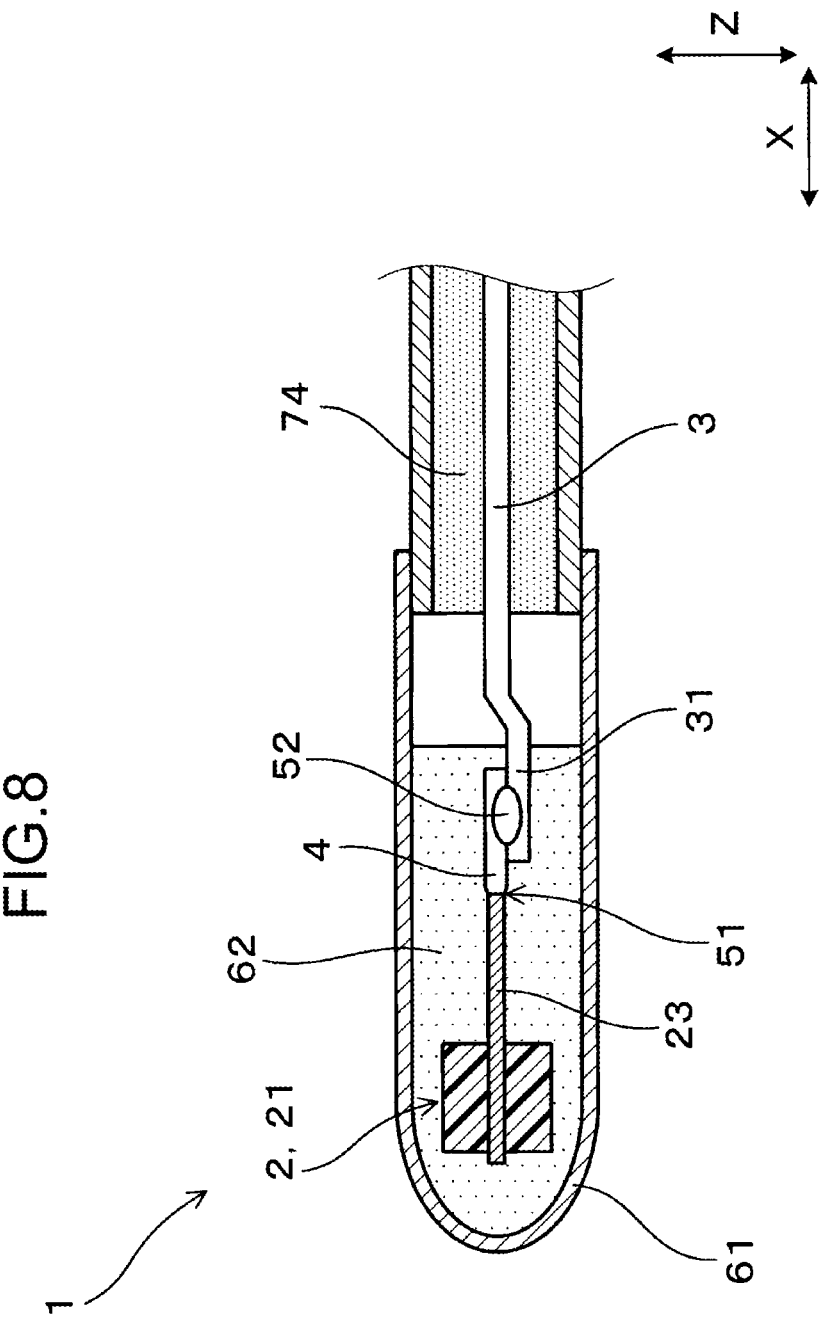

TEMPERATURE SENSOR

This application is the U.S. national phase of International Application No. PCT/JP2016/060887 filed Apr. 1, 2016 which designated the U.S. and claims priority to JP Patent Application No. 2015-076875 filed Apr. 3, 2015, and No. 2016-046037 filed Mar. 9, 2016,the entire contents of each of which are hereby incorporated by reference.

TECHNICAL FIELD

The present invention relates to a temperature sensor including a temperature-sensing element.

BACKGROUND ART

For example, a vehicle such as an automobile is equipped with an exhaust gas purification device for purifying exhaust gas generated in an internal combustion engine. The exhaust gas purification device includes a temperature sensor that detects the temperature of exhaust gas, and performs control on the basis of the temperature detected by the temperature sensor so as to reduce exhaust emissions.

The temperature sensor for use in the exhaust gas purification device is exemplified in Patent Literature 1. The temperature sensor of Patent Literature 1 includes a temperature-sensing element for detecting temperature, a pair of element electrode wires extending from the temperature-sensing element, and a pair of lead wires electrically connected to the pair of element electrode wires. Each of the element electrode wires is made of a Pt (platinum)-based alloy containing strontium, and formed in a rod-like shape. Each of the lead wires is made of a stainless alloy, and formed in a rod-like shape. The pair of element electrode wires and the pair of lead wires are bonded to each other by being welded together in such a manner that they overlap each other in the direction orthogonal to the axial direction thereof.

CITATION LIST

Patent Literature

Patent Literature 1: JP 2010-32493 A

SUMMARY OF INVENTION

Technical Problem

In the temperature sensor indicated in Patent Literature 1, however, materials having different linear expansion coefficients are used in the element electrode wire and the lead wire. In particular, if the element electrode wire and the lead wire are bonded together in a wide range as viewed in the axial direction, the bond part may be subjected to significant stress due to their large difference in axial thermal expansion. In recent years, the temperature of exhaust gas has shown a tendency to increase with a rise in output per unit displacement of an internal combustion engine used in an automobile or the like, and durability against further changes in temperature has been required.

The present invention has been made in consideration of the above background, and an object thereof is to provide a temperature sensor capable of improving the reliability of connection between an element electrode wire and a lead wire.

Solution to Problem

A temperature sensor according to an aspect of the present invention includes: a temperature detector including a temperature-sensing element for detecting temperature; a pair of element electrode wires each made of a noble metal or a noble metal alloy, one end being buried in the temperature detector, the other end being extended in the same direction as that of the other element electrode wire; a pair of lead wires each made of a Ni-based alloy or an Fe-based alloy, electrically connected to the element electrode wire, and formed to extend in an extending direction of the element electrode wire; and a pair of intermediate members each made of a Ni-based alloy or an Fe-based alloy, configured to electrically connect the element electrode wire to the lead wire, and formed to extend in the extending direction.

The element electrode wire and the intermediate member are provided in a line with each other in the extending direction. They are welded together in such a manner that opposing surfaces facing each other abut against each other to constitute an element-side weld.

The intermediate member and the lead wire are provided adjacent to each other in a direction orthogonal to the extending direction. They are welded together such that they overlap each other to constitute a lead-side weld.

The lead wire is extended closer to the temperature detector than the element-side weld is located.

A gap between the element electrode wire and the lead wire at least in the direction orthogonal to the extending direction is filled with filler, and the element electrode wire, the element-side weld, and the lead wire are fixed to one another by the filler.

Effect of Invention

In the temperature sensor, the element electrode wire and the intermediate member are provided in a line with each other in the extending direction. They are welded together in such a manner that the opposing surfaces facing each other abut against each other to constitute the element-side weld. Each of the opposing surfaces is one end of the element electrode wire/intermediate member in the extending direction. In this case, the region of the bond part can be formed in a small range, as compared with a case where the element electrode wire and the lead wire are bonded together on the outer peripheral surface along the extending direction. Consequently, the difference in thermal expansion between the element electrode wire and the intermediate member can be reduced, and the generation of stress can be reduced. Therefore, the reliability of connection between the element electrode wire and the intermediate member can be improved.

Each of the lead wire and the intermediate member is made of a Ni-based alloy or an Fe-based alloy. Consequently, the cost of the temperature sensor can be reduced. Since the lead wire and the intermediate member are formed of the same type of material, the work of bonding the lead wire to the intermediate member can be easily performed, and the bonding strength can be improved. In addition, there is no difference between the linear expansion coefficients of the lead wire and the intermediate member. Therefore, it is possible to prevent stress from occurring between the lead wire and the intermediate member when they are thermally expanded with changes in temperature. Thus, the reliability of connection between the lead wire and the intermediate member can also be ensured.

The lead wire is extended closer to the distal end side than the element-side weld is located. The gap between the element electrode wire and the lead wire at least in the direction orthogonal to the extending direction is filled with the filler. The element electrode wire, the element-side weld, and the lead wire are fixed to one another by the filler. Therefore, the lead wire having more strength than the element electrode wire plays a role as a splint, that is, plays a role in increasing the stiffness of the portion of the entire temperature sensor between the element-side weld and the temperature detector. As a result, it is possible to prevent the element electrode wire from being deformed due to vibration or the like, and prevent the element-side weld from being embrittled due to the stress applied thereto. Furthermore, since the filler is interposed between the element electrode wire and the lead wire, the element electrode wire and the lead wire can be prevented from interfering with each other. Therefore, the durability of the element electrode wire can be further improved. Consequently, the reliability of connection between the element electrode wire and the lead wire can be improved.

As described above, according to the present invention, it is possible to provide the temperature sensor capable of improving the reliability of connection between the element electrode wire and the lead wire.

BRIEF DESCRIPTION OF DRAWING

FIG. 7 shows a partial sectional view illustrating a distal end of a temperature sensor according to an Embodiment 2; and FIG. 8 shows a sectional view taken along a line VIII-VIII of FIG. 7.

DESCRIPTION OF EMBODIMENT

A temperature sensor can be used for measuring the temperature of exhaust gas flowing through an exhaust pipe in an exhaust gas purification system for purifying exhaust gas discharged from an internal combustion engine of an automobile. Various types of control of the exhaust gas purification system can be performed in accordance with the temperature measured with the temperature sensor.
[Embodiment]
(Embodiment 1)

An embodiment of a temperature sensor will be described using FIGS. 1 to 4.

Figure 1:
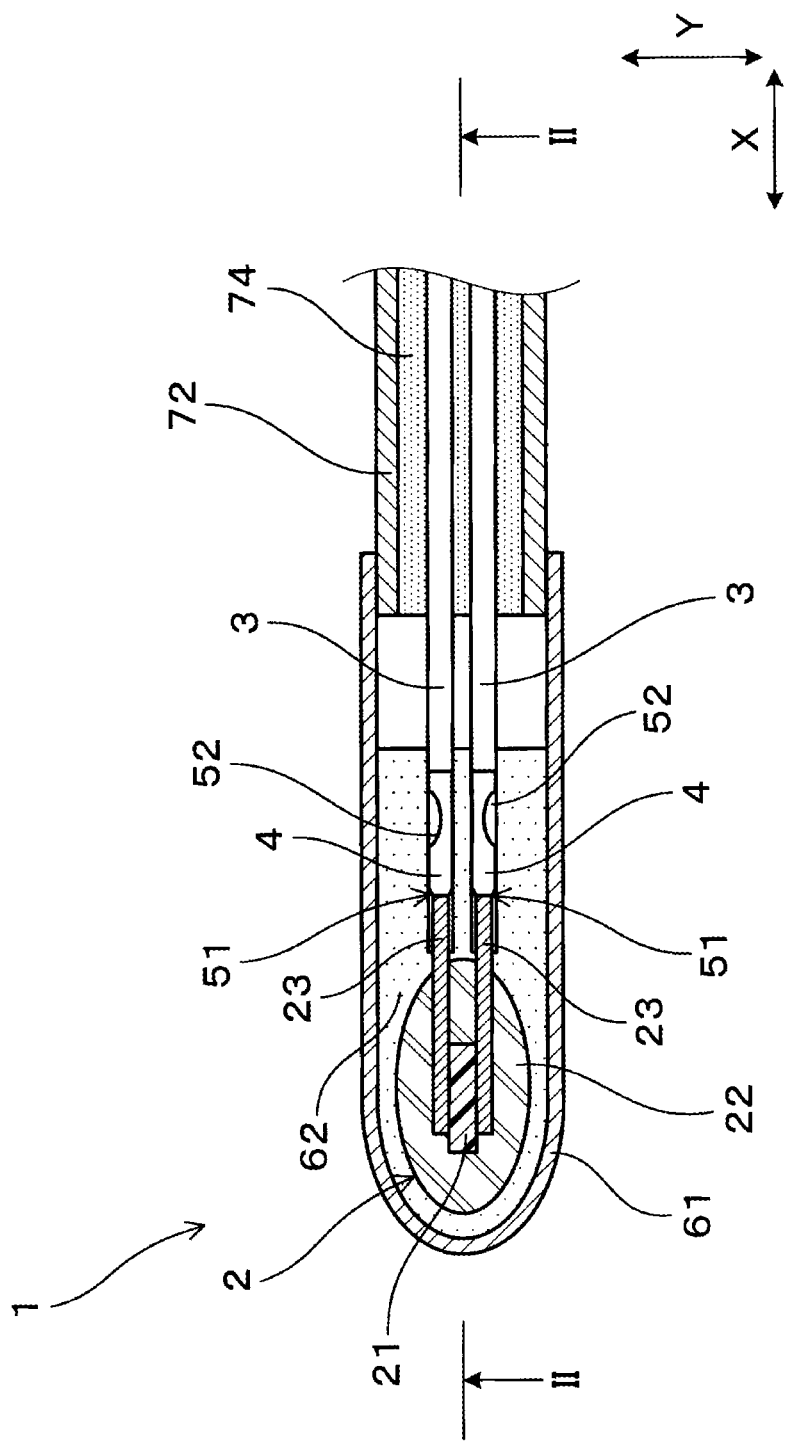
FIG. 1 shows a partial sectional view illustrating a distal end of a temperature sensor according to an Embodiment 1.
Figure 2:
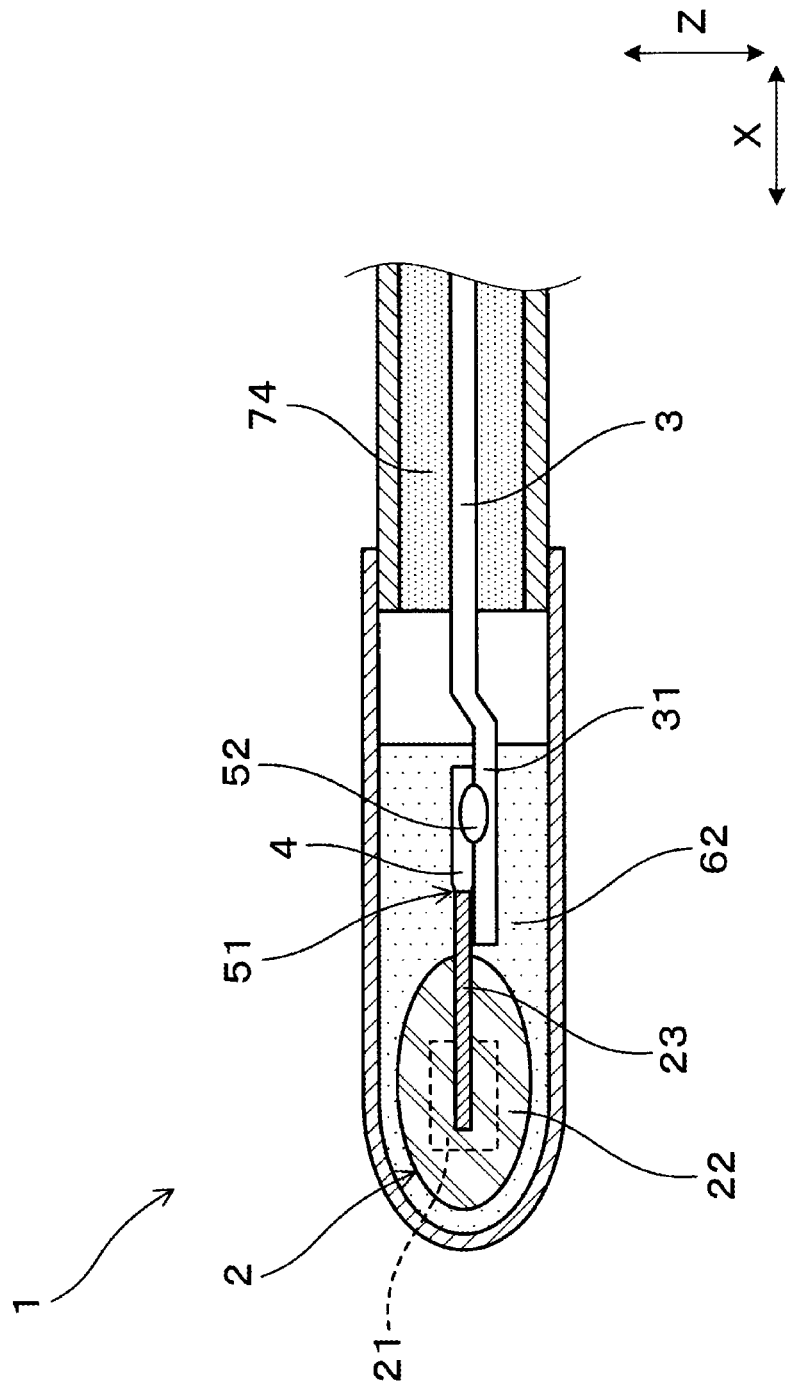
FIG. 2 shows a sectional view taken along a line II-II of FIG. 1.

A temperature sensor 1 according to the present embodiment includes, as illustrated in FIGS. 1 and 2, a temperature detector 2, a pair of element electrode wires 23, a pair of lead wires 3, and a pair of intermediate members 4. The temperature detector 2 includes a temperature-sensing element 21 for detecting temperature. Each of the element electrode wires 23 is made of a noble metal or a noble metal alloy, one end of which is buried in the temperature detector 2, and another end is extended in the same direction as that of the other element electrode wire 23. Each of the lead wires 3 is made of a Ni-based alloy or an Fe-based alloy, electrically connected to the element electrode wire 23, and is formed to extend in an extending direction X of the element electrode wire 23. Each of the intermediate members 4 is made of a Ni-based alloy or an Fe-based alloy, configured to electrically connect the element electrode wire 23 to the lead wire 3, and is formed to extend in the extending direction X.

The element electrode wire 23 and the intermediate member 4 are provided in a line with each other in the extending direction X. The element electrode wire 23 and the intermediate member 4 are welded together in such a manner that opposing surfaces 231, 41 facing each other abut against each other to constitute an element-side weld 51. As illustrated in FIG. 2, the intermediate member 4 and the lead wire 3 are provided adjacent to each other in the direction orthogonal to the extending direction X. The intermediate member 4 and the lead wire 3 are welded together such that they overlap each other to constitute a lead-side weld 52. The lead wire 3 is extended closer to the distal end side than the element-side weld 51 is located. A gap between the element electrode wire 23 and the lead wire 3 at least in the direction orthogonal to the extending direction X is filled with a filler 62. The element electrode wire 23, the element-side weld 51, and the lead wire 3 are fixed to one another by the filler 62. The shortest distance L, which is illustrated in FIG. 4, in the extending direction X between the element-side weld 51 and the lead-side weld 52 is equal to or greater than 0.1 mm. Note that the specific shape of the lead-side weld 52 is not illustrated in FIGS. 1 to 4.

In the description of the present embodiment, as illustrated in FIGS. 1 and 2, in the extending direction X of the element electrode wire 23, a side on which the temperature detector 2 is provided is referred to as a distal end side, and another side opposite to the distal end side is referred to as a proximal end side. In addition, a direction orthogonal to the extending direction X and in which the pair of element electrode wires 23 is disposed adjacent to each other is referred to as a lateral direction Y, and another direction orthogonal to both the extending direction X and the lateral direction Y is referred to as a longitudinal direction Z.

Figure 3:
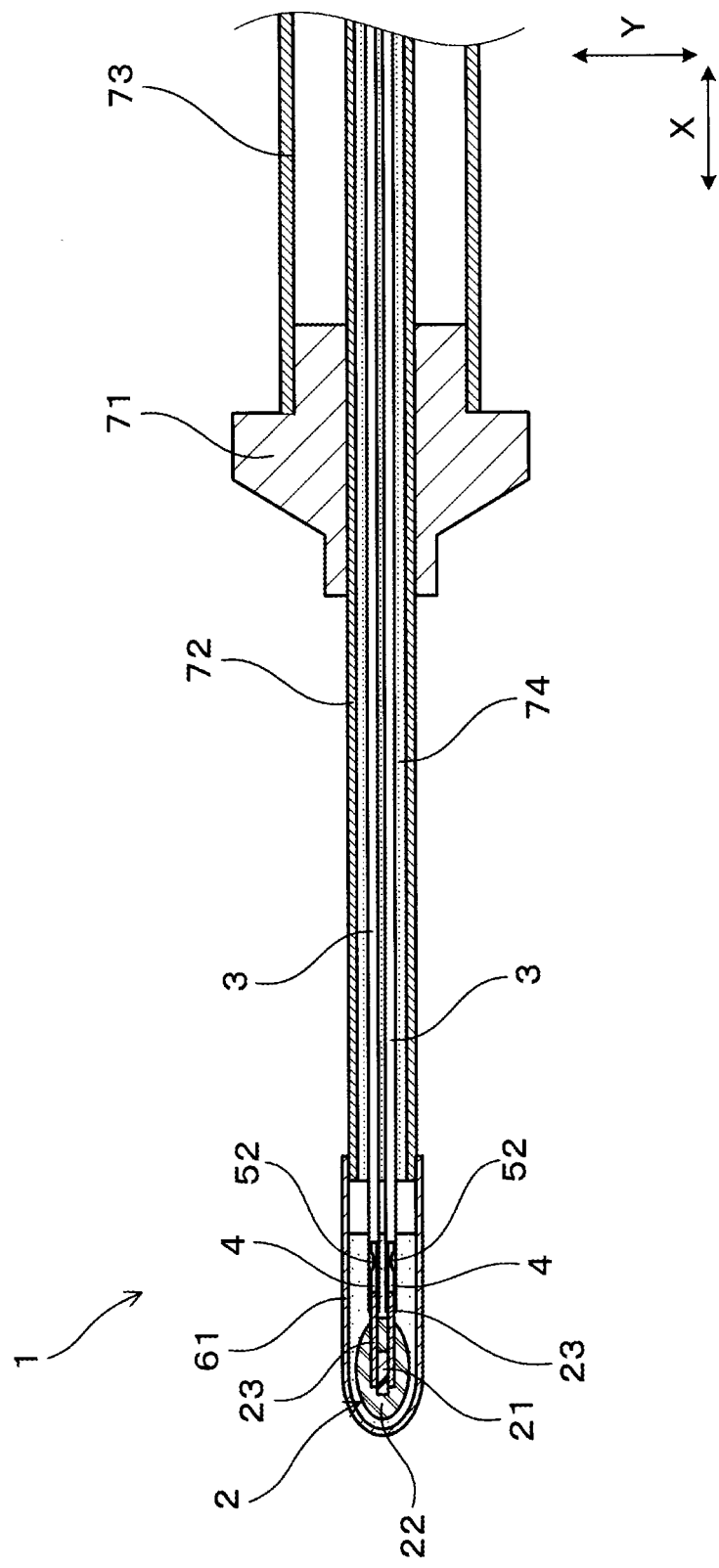
FIG. 3 shows a sectional view illustrating the temperature sensor according to the Embodiment 1.
Figure 4:
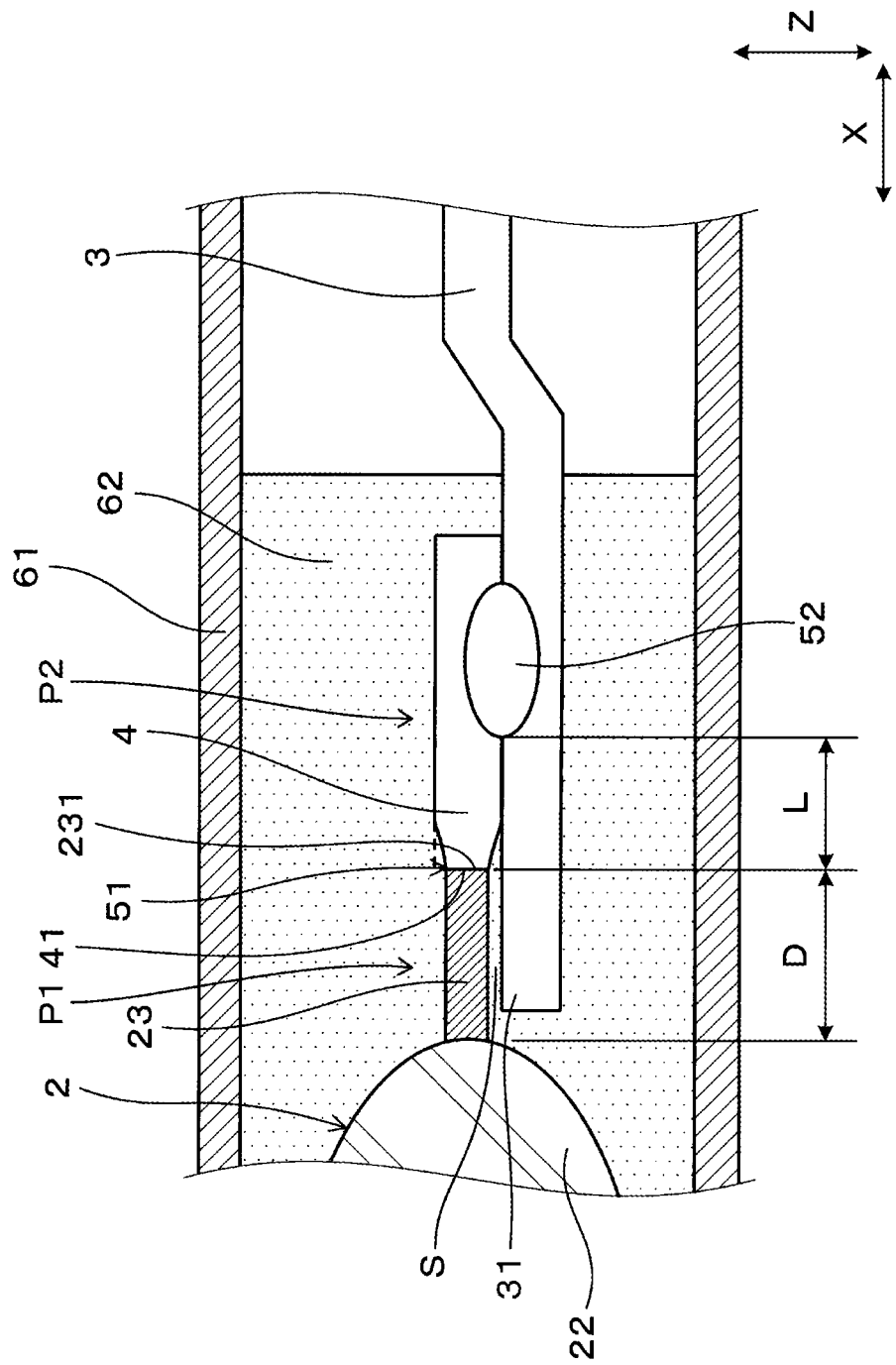
FIG. 4 shows a partial enlarged sectional view illustrating the temperature sensor according to the Embodiment 1.

As illustrated in FIG. 3, the temperature sensor 1 has an attachment part 71, a tubular member 72, and a case member 73. The attachment part 71 is fixed to an exhaust pipe (not illustrated) connected to an internal combustion engine. The tubular member 72 is inserted and held in the attachment part 71. The case member 73 is extended from the attachment part 71 toward the proximal end side.

The tubular member 72 has a cylindrical shape extending in the extending direction X. The distal end of the tubular member 72 is provided with a cover member 61 having a cylindrical shape. One end of the cover member 61 is closed so that the cover member 61 has a bottomed cylindrical shape.

The pair of lead wires 3 is inserted and disposed in the tubular member 72. Each of the lead wires 3 has a columnar shape extending in the extending direction X, and a connection end 31 is formed at the distal end thereof so as to be connected to the intermediate member 4. As illustrated in FIGS. 2 and 4, the connection end 31 is provided such that it is not aligned with the central axis of the proximal end portion of the lead wire 3 in the longitudinal direction Z. At the proximal end of the pair of lead wires 3, a connection terminal (not illustrated) is formed so as to be connected to an external connection wire of an external device. A gap between the pair of lead wires 3 and the tubular member 72 is filled with a body-side filler 74 having an electric insulating property, whereby the pair of lead wires 3 is fixed in the tubular member 72, with the gap between the pair of lead wires 3 and the tubular member 72 insulated. The distal end of each of the lead wires 3 is disposed at a position which is closer to the distal end side, that is, closer to the temperature detector 2, than the position of the tubular member 72 is.

Each of the lead wires 3 is formed of a Fe—Cr-based alloy, and has a coefficient of thermal expansion E4 of $15 \times 10^{-6}$/K.

As illustrated in FIGS. 1, 2, and 4, the intermediate member 4 bonded to the connection end 31 of the corresponding lead wire 3 has a columnar shape formed to extend in the extending direction X. In the present embodiment, as illustrated in FIGS. 2 and 4, each intermediate member 4 overlaps the connection end 31 of the connected lead wire 3 in the longitudinal direction Z. Then, the intermediate member 4 and the connection end 31 are welded together at one point to form the lead-side weld 52. Alternatively, each intermediate member 4 and the corresponding lead wire 3 may be welded together at a plurality of points. In a section orthogonal to the extending direction X, an outline of the intermediate member 4 is larger than an outline of the element electrode wire 23, and the outline of the element electrode wire 23 is within the outline of the intermediate member 4 when viewed in the extending direction X. Note that the present invention is not limited thereto and the outline of the element electrode wire 23 may be larger than or identical to the outline of the intermediate member 4 in the section orthogonal to the extending direction X. The intermediate member 4 is formed of a Fe—Cr-based alloy, and has a coefficient of thermal expansion E3 of $15 \times 10^{-6}$/K.

In the present embodiment, the intermediate member 4 and the lead wire 3 are formed of the same type of material. As the Fe-based alloy for use in the pair of lead wires 3 and the pair of intermediate members 4, for example, an alloy containing Fe as a base material and 11-26 wt % Cr can be used. In addition to Cr, Ni or Al (aluminum) may be contained. Examples of such an Fe-based alloy can include Fe—Cr—Al, SUS310S, and the like. Such an Fe-based alloy can exhibit excellent heat resistance even at a high temperature of around 900° C. As the Ni-based alloy for use in the pair of lead wires 3 and the pair of intermediate members 4, for example, an alloy containing Ni as a base material and 14-25 wt % Cr can be used. In addition to Cr, Fe or Al may be contained. Examples of such a Ni—Cr-based alloy can include NCF600, NCF601, and the like. Such a Ni—Cr-based alloy can exhibit excellent heat resistance even at a high temperature of around 1100° C.

As illustrated in FIGS. 1, 2, and 4, the pair of element electrode wires 23 extending from the temperature detector 2 is connected to the pair of intermediate members 4. Each element electrode wire 23 is provided in a line with the connected intermediate member 4 in the extending direction X, and each element electrode wire 23 and the connected intermediate member 4 are welded together such that they abut against each other. Consequently, the element-side weld 51 is formed.

As illustrated in FIG. 4, the connection end 31 of the lead wire 3 is extended to a position where the connection end 31 overlaps the element electrode wire 23 in the longitudinal direction Z. Specifically, the connection end 31 of the lead wire 3 is extended to a region which is closer to the distal end side than the element-side weld 51 is. The connection end 31 of the lead wire 3 is also extended close to the temperature-sensing element 21. More specifically, the connection end 31 of the lead wire 3 is extended to the vicinity of an enclosing part 22 made of glass, which will be described later. The connection end 31 of the lead wire 3 is extended to a position which is closer to the distal end side than the center in the extending direction X of the portion of the element electrode wire 23 projecting from the temperature detector 2 is. The element electrode wire 23 and the lead wire 3 face each other with a substantially fixed space therebetween in the longitudinal direction Z. Preferably, the connection end 31 of the lead wire 3 is extended as close as possible to the enclosing part 22.

The shortest distance L in the extending direction X between the element-side weld 51 and the lead-side weld 52 is preferably equal to or greater than 0.1 mm. In the present embodiment, in particular, the shortest distance L is equal to or greater than 0.2 mm. More specifically, the element-side weld 51 and the lead-side weld 52 are formed at such positions that the shortest distance L in the extending direction X is 0.2 mm.

In a case where the intermediate member 4 and the connection end 31 of the lead wire 3 are welded together at a plurality of points, a plurality of lead-side welds 52 is formed between them. The shortest distance L for this case is the shortest distance in the extending direction X between the element-side weld 51 and the lead-side weld 52 provided closest to the element-side weld 51 of the plurality of lead-side welds 52. In terms of cost reduction, improvement in vibration resistance, and the like, the shortest distance L is preferably equal to or less than 1.0 mm, and more preferably equal to or less than 0.8 mm.

As illustrated in FIGS. 1 and 2, the temperature detector 2 has the temperature-sensing element 21 and the enclosing part 22. The temperature-sensing element 21 includes a temperature-measuring resistor. The temperature-sensing element 21 and the distal end side of the pair of element electrode wires 23 are held inside the enclosing part 22. As illustrated in FIG. 4, the length dimension D of the element electrode wire 23 in the extending direction X from the temperature detector 2 to a portion projecting toward the lead wire 3 is preferably equal to or greater than 0.1 mm. In the present embodiment, in particular, the length dimension D is equal to or greater than 0.2 mm. More specifically, the temperature detector 2 and the element-side weld 51 are provided such that the length dimension D is 0.2 mm. In terms of cost reduction, improvement in vibration resistance, and the like, the length dimension D is preferably equal to or less than 1.0 mm, and more preferably equal to or less than 0.8 mm. As illustrated in FIGS. 1 and 2, the temperature detector 2 is housed in the cover member 61 that covers the temperature detector 2 from the distal end side and an outer peripheral side. The temperature detector 2 and the cover member 61 are fixed by the filler 62 filled inside the cover member 61. The filler 62 is made of $Al_2O_3$ containing glass or MgO containing glass. The filler 62 containing glass can increase the stiffness of a portion of the entire temperature sensor 1 between the element-side weld 51 and the distal end side. The filler 62 within the cover member 61 extends from the distal end side of the temperature detector 2 to a position which is closer to the proximal end side than the position of the lead-side weld 52 is.

As illustrated in FIG. 4, a region S in the longitudinal direction Z between the element electrode wire 23 and the connection end 31 of the lead wire 3 is also filled with the filler 62. Consequently, the element electrode wire 23, the element-side weld 51, the intermediate member 4, and the lead wire 3 are fixed to one another by the filler 62. The element electrode wire 23 and the connection end 31 of the lead wire 3 face each other in the longitudinal direction Z via the filler 62.

A sectional area of a section of the filler 62 orthogonal to the extending direction X at a portion P1 where the element electrode wire 23 overlaps the lead wire 3 in the longitudinal direction Z is substantially equal to that at a portion P2 where the intermediate member 4 overlaps the lead wire 3 in the longitudinal direction Z.

As illustrated in FIG. 1, in the vicinity of the distal end of the pair of element electrode wires 23, the temperature-sensing element 21 is sandwiched and fixed between the pair of element electrode wires 23 provided in parallel with each other. The temperature-sensing element 21 and the pair of element electrode wires 23 are baked and bonded to each other in advance using a noble metal paste containing glass frit. The temperature-sensing element 21 and the distal end portion of the pair of element electrode wires 23 baked and bonded to each other are held inside the enclosing part 22 made of glass.

The element electrode wire 23 is made of Pt, a Pt-based alloy containing at least one of Ir, Rh, and Sr, or dispersion-strengthened Pt containing metallic particles including Pt and oxide particles dispersed among the metallic particles. The oxide particles can be, for example, zirconia. In the present embodiment, each of the element electrode wires 23 is made of a Pt-based alloy, and formed in a columnar shape extending in the extending direction X. As the Pt-based alloy, an alloy containing Pt as a base material and 5-25 wt % Ir (iridium) is used. Each of the element electrode wires 23 according to the present embodiment has a coefficient of thermal expansion E2 of $9 \times 10^{-6}$/K, which is substantially equal to the coefficient of thermal expansion E1 of the temperature-sensing element 21. The coefficient of thermal expansion of the enclosing part 22 is set equal to the coefficient of thermal expansion of the temperature-sensing element 21. The coefficient of thermal expansion E2 of the element electrode wire 23, the coefficient of thermal expansion E3 of the intermediate member 4, and the coefficient of thermal expansion E4 of the lead wire 3 satisfy the relation E2≤E3≤E4. In particular, in the present embodiment, the coefficient of thermal expansion E3 of the intermediate member 4 and the coefficient of thermal expansion E4 of the lead wire 3 satisfy the relation E3=E4. Note that a Pt-based alloy containing Pt as a base material and 5-15 wt % Rh can also be used as the element electrode wire 23 instead of the Pt-based alloy containing Ir.

Next, the bonding between the element electrode wire 23, the intermediate member 4, and the lead wire 3 will be described.

First, the pair of element electrode wires 23 extending from the temperature detector 2 is bonded to the pair of intermediate members 4. The element electrode wire 23 and the intermediate member 4 are provided in a line with each other in the extending direction X, and bonded together by means of butt welding that is performed while the opposing surfaces 231, 41 facing each other abut against each other. In this manner, the intermediate member 4 and the element electrode wire 23 are bonded together before the intermediate member 4 and the lead wire 3 are bonded together, whereby the alignment work of disposing the intermediate member 4 and the element electrode wire 23 in a line with each other in the extending direction X can be easily performed. If the intermediate member 4 and the lead wire 3 are bonded together first, the pair of intermediate members 4 needs to be simultaneously aligned with the pair of element electrode wires 23, which makes the alignment work difficult. The difficulty of the alignment work leads to significant manufacturing variations in the quality of welding, and thus the reliability of welding can hardly be ensured. As a result, a defective bond may be formed between the pair of element electrode wires 23 and the pair of intermediate members 4. Other possible structures include disposing the pair of element electrode wires, the pair of intermediate members, and the pair of lead wires in a line with one another in the extending direction X to bond them together, and disposing the pair of element electrode wires and the pair of lead wires in a line with each other in the extending direction X to directly bond them together. However, the alignment work is still difficult to perform on these structures.

Next, the pair of intermediate members 4 connected to the pair of element electrode wires 23 is bonded to the pair of lead wires 3. The intermediate member 4 is disposed adjacent to the lead wire 3 in the longitudinal direction Z, and the intermediate member 4 and the lead wire 3 are bonded together in such a manner that they overlap each other in the longitudinal direction Z. In the present embodiment, the intermediate member 4 and the lead wire 3 are bonded together by means of laser welding.

Next, the effects of the present embodiment will be described.

In the temperature sensor 1, the element electrode wire 23 and the intermediate member 4 are provided in a line with each other in the extending direction X. The element electrode wire 23 and the intermediate member 4 are welded together in such a manner that the opposing surfaces 231, 41 facing each other abut against each other to constitute the element-side weld 51. Therefore, the reliability of connection between the element electrode wire 23 and the intermediate member 4 can be improved. For example, suppose the element electrode wire 23 and the intermediate member 4 are welded together such that they overlap each other in the longitudinal direction Z, in contrast to the case of the present embodiment. In this case, a cutout is formed between the element electrode wire 23 and the intermediate member 4 in such a shape that a part between the element electrode wire 23 and the intermediate member 4 is sharply cut. Then, stress may be concentrated at the cutout. In contrast, in the present embodiment, the element electrode wire 23 and the intermediate member 4 are bonded together by means of butt welding as mentioned above. Therefore, the element electrode wire 23 and the intermediate member 4 can be structured such that the above-mentioned cutout is not created therebetween. Consequently, it is possible to avoid the concentration of stress due to the difference in thermal expansion between the element electrode wire 23 and the intermediate member 4.

Each of the lead wire 3 and the intermediate member 4 is made of a Ni-based alloy or an Fe-based alloy. Consequently, the cost of the temperature sensor 1 can be reduced. Since the lead wire 3 and the intermediate member are formed of the same type of material, the work of bonding the lead wire 3 to the intermediate member 4 can be easily performed, and the bonding strength can be improved. In addition, there is no difference between the linear expansion coefficients of the lead wire 3 and the intermediate member 4. Therefore, it is possible to prevent stress from occurring between the lead wire 3 and the intermediate member 4 when they are thermally expanded with changes in temperature. Thus, the reliability of connection between the lead wire 3 and the intermediate member 4 can also be ensured.

The lead wire 3 is extended closer to the distal end side than the element-side weld 51 is located. The filler 62 is interposed between the element electrode wire 23 and the lead wire 3 at least in the longitudinal direction Z. The element electrode wire 23, the element-side weld 51, and the lead wire 3 are fixed to one another by the filler 62. Therefore, the lead wire 3 having more strength than the element electrode wire 23 plays a role as a splint, that is, plays a role in increasing the stiffness of the portion of the entire temperature sensor 1 between the element-side weld and the distal end side, and stress on the element electrode wire 23 and the element-side weld 51 due to vibration or the like can be suppressed from being applied. Furthermore, since the filler 62 is interposed between the element electrode wire 23 and the lead wire 3, the element electrode wire 23 and the lead wire 3 can be prevented from interfering with each other. Therefore, the durability of the element electrode wire 23 can be further improved. Consequently, the reliability of the element electrode wire 23 and the element-side weld 51 can be improved.

The shortest distance L in the extending direction X between the element-side weld 51 and the lead-side weld 52 is equal to or greater than 0.1 mm. Consequently, the concentration of stress at the element-side weld 51 can be avoided, and the reliability of connection between the element electrode wire 23 and the element-side weld 51 can be improved. Specifically, since the above-mentioned cutout can exist in the vicinity of the lead-side weld 52, the concentration of stress is relatively likely to occur in the vicinity of the lead-side weld 52. Therefore, the shortest distance L is set equal to or greater than 0.1 mm, thereby avoiding the formation of the element-side weld 51 in the region where the concentration of stress is likely to occur. Consequently, the concentration of stress at the element-side weld 51 can be avoided.

In the present embodiment, the shortest distance L is equal to or greater than 0.2 mm. Consequently, the reliability of connection of the element-side weld 51 can be further improved.

The length dimension D of the element electrode wire 23 from the temperature detector 2 to the portion projecting toward the lead wire 3 is equal to or greater than 0.1 mm. Consequently, the reliability of connection of the element-side weld 51 can be improved. Specifically, stress from the enclosing part 22 is relatively likely to be concentrated at the root of the element electrode wire 23 projecting from the enclosing part 22. Therefore, the length dimension D is set equal to or greater than 0.1 mm, thereby avoiding the formation of the element-side weld 51 in the region where the concentration of stress is likely to occur. Consequently, the concentration of stress at the element-side weld 51 can be avoided.

In the present embodiment, the length dimension D is equal to or greater than 0.2 mm. Therefore, the reliability of connection of the element electrode wire 23 and the element-side weld 51 can be further improved. Furthermore, the highly durable temperature sensor 1 can be easily manufactured. If the element-side weld 51 is in contact with or disposed inside the temperature detector 2 (enclosing part 22), thermal stress may be generated due to the difference in thermal expansion between the temperature detector 2 (enclosing part 22) and the element-side weld 51, and cause damage to the temperature detector 2 (enclosing part 22). Therefore, the length dimension D is set equal to or greater than 0.2 mm, whereby the element-side weld 51 can be prevented from being in contact with or disposed inside the temperature detector 2 (enclosing part 22) even in consideration of dimensional variations, and damage to the temperature detector 2 can be prevented.

Further, the element electrode wire 23 is made of Pt, a Pt-based alloy containing at least one of Ir, Rh, and Sr, or dispersion-strengthened Pt containing metallic particles including Pt and oxide particles dispersed among the metallic particles. Therefore, the strength of the element electrode wire 23 is easily improved. Consequently, embrittlement of the element electrode wire 23 due to the heat for welding the element electrode wire 23 and the intermediate member 4 is easily suppressed from occurring. Accordingly, the reliability of connection between the element electrode wire 23 and the lead wire 3 can be easily ensured.

The temperature detector 2 is housed in the cover member 61, and the temperature detector 2 and the cover member 61 are fixed to each other by the filler 62 filled inside the cover member 61. Consequently, the temperature detector 2 can be prevented from vibrating relative to the cover member 61.

Meanwhile, the element-side weld 51 may be subjected to stress due to the expansion and contraction of the cover member 61 caused by changes in temperature. In particular, when the cover member 61 is contracted, the temperature detector 2 is pushed through the filler 62 toward the proximal end side in the extending direction X, and the element-side weld 51 is accordingly subjected to the stress that causes the element electrode wire 23 to push the intermediate member 4.

However, since the element-side weld 51 is formed in such a manner that the element electrode wire 23 and the intermediate member 4 are disposed in a line with each other in the extending direction X and bonded together, force on the element-side weld 51 in the direction of separating the element electrode wire 23 and the intermediate member 4 can be suppressed from being applied. Therefore, even though the temperature detector 2 is configured to be housed in the cover member 61 and fixed by the filler 62, the reliability of connection between the element electrode wire 23 and the lead wire 3 can be effectively improved.

The sectional area of the section of the filler 62 orthogonal to the extending direction X at the portion P1 where the element electrode wire 23 overlaps the lead wire 3 in the longitudinal direction Z is equal to that at the portion P2 where the intermediate member 4 overlaps the lead wire 3 in the longitudinal direction Z. This configuration prevents air from remaining at the distal end of the cover member 61 when the filler 62 is filled into the distal end of the cover member 61 through the proximal end side thereof, dried, and sintered. Therefore, the filling ratio of the filler 62 inside the distal end of the cover member 61 is easily enhanced. Consequently, the fixing force that is applied by the filler 62 to the element electrode wire 23, the element-side weld 51, and the lead wire 3 can be enhanced. Accordingly, the reliability of the element electrode wire 23 and the element-side weld 51 can be improved.

As described above, according to the present embodiment, it is possible to provide the temperature sensor capable of improving the reliability of connection between the element electrode wire and the lead wire.

(Confirmation Test 1)

In the present confirmation test, cooling/heating, thermal shock, and vibration tests were conducted using samples 1 to 5, i.e., temperature sensors having the same basic configuration indicated in Embodiment 1 and having different shortest distances L. Then, the reliability of connection between the element electrode wire 23 and the lead wire 3 of each sample was evaluated.

Specifically, samples 1 to 5 satisfied L=0 mm, 0.05 mm, 0.1 mm, 0.2 mm, and 0.3 mm, respectively. The length dimension D of the element electrode wire 23 in the extending direction X from the temperature detector 2 to the portion projecting toward the lead wire 3 was 0.2 mm in any of the samples. Note that sample 4 is the temperature sensor 1 indicated in Embodiment 1.

In the cooling/heating test, each sample was alternately exposed to a normal temperature atmosphere (25° C.) and a high temperature atmosphere (950° C.). With regard to the test cycle, 10,000 cycles were conducted, with the process of keeping a sample in one of the atmospheres for two minutes and keeping it in the other atmosphere for another two minutes counted as one cycle.

In the thermal shock test, each sample was heated and rapidly cooled by a blower. In the present test, each sample was heated to 950° C. and cooled to 25° C. at a maximum cooling rate of 300° C. per second. With regard to the test cycle, 10,000 cycles were conducted, with the process of heating and cooling counted as one cycle.

In the vibration test, each sample was placed in a high temperature atmosphere (950° C.) and subjected to a vibration load. The vibration acceleration on each sample was 40 G, and the vibration frequency was swept around a resonance point in the temperature detector 2. The test was conducted for 100 hours.

The results of the cooling/heating, thermal shock and vibration tests are indicated in Table 1. Each cross mark "x" in the table indicates that a disconnection or indication of disconnection was observed between the element electrode wire and the lead wire after the test. Each circle mark "○" indicates that the connection between the element electrode wire and the lead wire was normal even after the test. A disconnection or indication of disconnection was confirmed, for example, by measuring the change in sensor output (electrical resistance) after the test.

TABLE 1

| | L [mm] | Cooling/Heating Test | Thermal Shock Test | Vibration Test |
| --- | --- | --- | --- | --- |
| Sample 1 | 0 | x | x | x |
| Sample 2 | 0.05 | x | x | ○ |
| Sample 3 | 0.1 | ○ | ○ | ○ |
| Sample 4 | 0.2 | ○ | ○ | ○ |
| Sample 5 | 0.3 | ○ | ○ | ○ |

As can be seen from Table 1, after any of the cooling/heating, thermal shock, and vibration tests on sample 1, a disconnection or indication of disconnection was observed between the element electrode wire and the lead wire. In each of the cooling/heating and thermal shock tests on sample 2, a disconnection or indication of disconnection was observed between the element electrode wire and the lead wire. In contrast, after any of the cooling/heating, thermal shock, and vibration tests on each of samples 3 to 5, which satisfied shortest distance L≥0.1, the connection between the element electrode wire 23 and the lead wire 3 was normal.

It can be understood from these results that the reliability of connection between the element electrode wire 23 and the lead wire 3 can be improved when the shortest distance L in the extending direction X to the lead-side weld 52 where the intermediate member 4 is bonded to the lead wire 3 is equal to or greater than 0.1 mm.

(Confirmation Test 2)

In the present confirmation test, the cooling/heating test was conducted using samples 6 to 9, i.e., temperature sensors having the same basic configuration indicated in Embodiment and having different length dimensions D. Then, the reliability of connection between the element electrode wire 23 and the lead wire 3 of each sample was evaluated.

Sample 6 to 9 satisfied D=0 mm, 0.05 mm, 0.1 mm, and 0.2 mm, respectively. The shortest distance L in the extending direction X between the element-side weld 51 and the lead-side weld 52 was 0.2 mm in any of the samples.

The test conditions and evaluation method for the present test are similar to those for the cooling/heating test conducted in Confirmation Test 1. The results are indicated in Table 2.

TABLE 2

| | D [mm] | Cooling/Heating Test |
| --- | --- | --- |
| Sample 6 | 0 | x |
| Sample 7 | 0.05 | x |
| Sample 8 | 0.1 | ○ |
| Sample 9 | 0.2 | ○ |

As can be seen from Table 2, in each of samples 6 and 7, a disconnection or indication of disconnection was observed between the element electrode wire and the lead wire. In contrast, in each of samples 8 and 9, which satisfied length dimension D≥0.1, the connection between the element electrode wire 23 and the lead wire 3 was normal.

It can be understood from these results that the reliability of connection between the element electrode wire 23 and the lead wire 3 can be improved when the length dimension D of the element electrode wire 23 in the extending direction X from the temperature detector 2 to the portion projecting toward the lead wire 3 is equal to or greater than 0.1 mm.

(Reference Embodiment)

Figure 5:
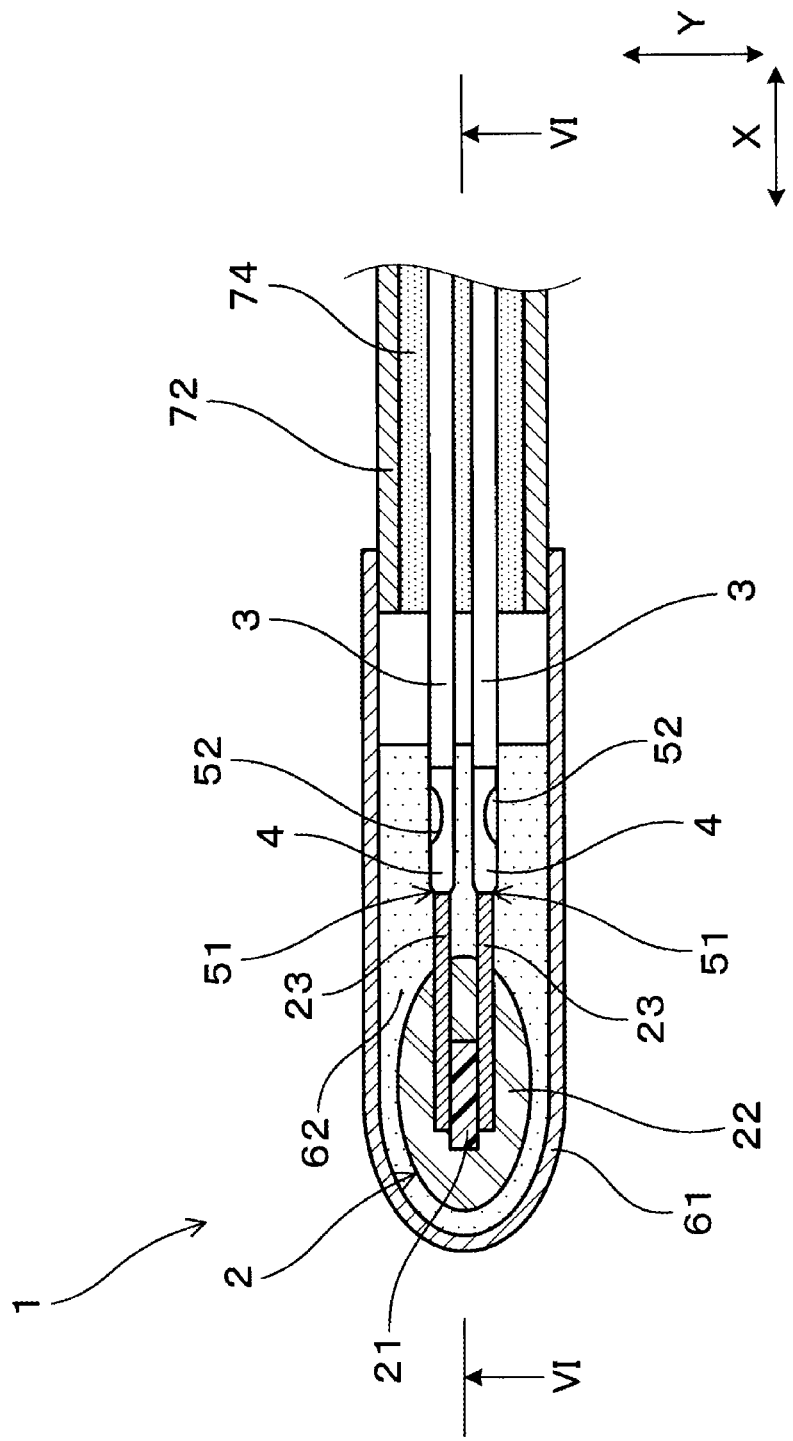
FIG. 5 shows a partial sectional view illustrating a distal end of a temperature sensor according to a Reference Embodiment.
Figure 6:
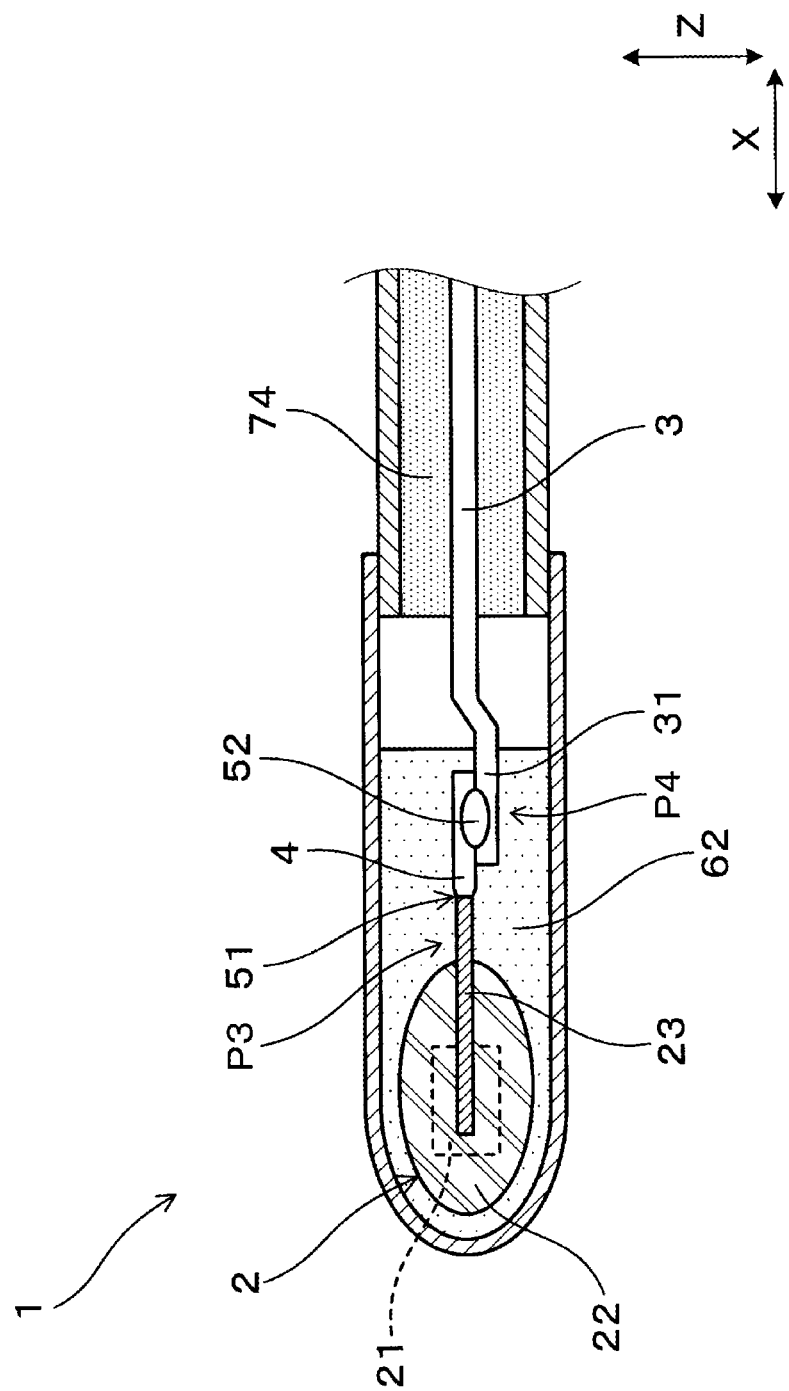
FIG. 6 shows a sectional view taken along a line VI-VI of FIG. 5.

In the present embodiment, as illustrated in FIGS. 5 and 6, the element-side weld 51 is disposed closer to the temperature detector 2 than the distal end of the lead wire 3 is. Specifically, the element-side weld 51 overlaps the lead wire 3 (connection end 31) in the longitudinal direction Z in Embodiment 1, whereas the element-side weld 51 does not overlap the lead wire 3 in the longitudinal direction Z in the present embodiment.

As illustrated in FIG. 6, the sectional area of the filler 62 orthogonal to the extending direction X at a portion P3 where the element electrode wire 23 projects from the temperature detector 2 in the extending direction X is larger than that at a portion P4 where the lead wire 3 and the intermediate member 4 extending in the extending direction X overlap each other in the longitudinal direction Z. Specifically, in the space within the cover member 61 without the filler 62, the sectional area orthogonal to the extending direction X at the portion P4 located on the proximal end side, i.e., the side through which the filler 62 is filled into the cover member 61, is smaller than that at the portion P3 located on the distal end side. Therefore, when the filler 62 is filled into the distal end of the cover member 61 through the proximal end side of the cover member 61, dried, and sintered, air remains at the distal end of the cover member 61. As a result, the filling rate of the filler 62 inside the distal end of the cover member 61 is liable to decrease. In contrast, in Embodiment 1, in the space within the cover member 61 without the filler 62, the sectional area orthogonal to the extending direction X at the portion P2 on the proximal end side of the cover member 61 is substantially equal to that at the portion P1 on the distal end side as illustrated in FIG. 4.

Therefore, the filling rate of the filler 62 inside the distal end of the cover member 61 is easily enhanced.

The other configurations are similar to those of Embodiment 1. Among the reference signs used in the present embodiment or in the drawings related to the present embodiment, the reference signs identical to those used in Embodiment 1 represent components or the like similar to those of Embodiment 1 unless otherwise indicated.

(Embodiment 2)

In the present embodiment, as illustrated in FIGS. 7 and 8, the structure of the temperature sensor 1 indicated in Embodiment 1 is partially changed.

The temperature detector 2 of the temperature sensor 1 according to the present embodiment is formed of the temperature-sensing element 21 having a columnar shape. The distal end portion of the element electrode wire 23 is buried in the temperature-sensing element 21. In the present embodiment, the enclosing part (reference sign 22 in FIGS. 1 to 4) described in Embodiment 1 or the like is not formed. Specifically, in the present embodiment, the filler 62 is directly filled around the temperature-sensing element 21.

The other configurations are similar to those of Embodiment 1. Among the reference signs used in the present embodiment or in the drawings related to the present embodiment, the reference signs identical to those used in Embodiment 1 represent components or the like similar to those of Embodiment 1 unless otherwise indicated.

The effects that can be obtained in the present embodiment are similar to those of Embodiment 1.

REFERENCE SIGN LIST

1: temperature sensor
2: temperature detector
21: temperature-sensing element
23: element electrode wire
3: lead wire
4: intermediate member
51: element-side weld
52: lead-side weld
62: filler
X: extending direction

The invention claimed is:

1. A temperature sensor comprising:
a temperature detector including a temperature-sensing element for detecting temperature;
a pair of element electrode wires each made of a noble metal or a noble metal alloy, one end being buried in the temperature detector, another end being extended in a same direction as that of the other element electrode wire;
a pair of lead wires each made of a Ni-based alloy or an Fe-based alloy, electrically connected to the element electrode wire, and formed to extend in an extending direction of the element electrode wire; and
a pair of intermediate members each made of a Ni-based alloy or an Fe-based alloy, configured to electrically connect the element electrode wire to the lead wire, and formed to extend in the extending direction, wherein
the element electrode wire and the intermediate member are provided in a line with each other in the extending direction, and welded together in such a manner that opposing surfaces facing each other abut against each other to constitute an element-side weld,
the intermediate member and the lead wire are provided adjacent to each other in a direction orthogonal to the extending direction, and welded together such that the intermediate member and the lead wire overlap each other to constitute a lead-side weld,
the lead wire is extended closer to the temperature detector than the element-side weld is located,
a gap between the element electrode wire and the lead wire at least in the direction orthogonal to the extending direction is filled with a filler, and
the element electrode wire, the element-side weld, and the lead wire are fixed to one another by the filler.

2. The temperature sensor according to claim 1, wherein a shortest distance L in the extending direction between the element-side weld and the lead-side weld is equal to or greater than 0.1 mm.

3. The temperature sensor according to claim 2, wherein the shortest distance L is equal to or greater than 0.2 mm.

4. The temperature sensor according to claim 1, wherein a length dimension D of the element electrode wire in the extending direction from the temperature detector to a portion projecting toward the lead wire is equal to or greater than 0.1 mm.

5. The temperature sensor according to claim 4, wherein the length dimension D is equal to or greater than 0.2 mm.

6. The temperature sensor according to claim 1, wherein the element electrode wire is made of Pt, a Pt-based alloy containing at least one of Ir, Rh, and Sr, or dispersion-strengthened Pt containing both metallic particles including Pt and oxide particles dispersed among the metallic particles.

7. The temperature sensor according to claim 1, wherein the temperature detector is housed in a cover member that covers the temperature detector from a distal end side and an outer peripheral side, and the temperature detector and the cover member are fixed to each other by the filler filled inside the cover member.

8. The temperature sensor according to claim 1, wherein a sectional area of a section of the filler orthogonal to the extending direction at a portion where the element electrode wire overlaps the lead wire in the direction orthogonal to the extending direction is equal to that at another portion where the intermediate member overlaps the lead wire in the direction orthogonal to the extending direction.

* * * * *

UNITED STATES PATENT AND TRADEMARK OFFICE
CERTIFICATE OF CORRECTION

PATENT NO. : 10,422,701 B2  
APPLICATION NO. : 15/563706  
DATED : September 24, 2019  
INVENTOR(S) : Ozeki et al.

Page 1 of 1

It is certified that error appears in the above-identified patent and that said Letters Patent is hereby corrected as shown below:

On the Title Page

At Column 1, Item (30) The Foreign Application Priority Data reads:  
Mar. 9, 2016 (JP) .........................2016-046037

The Foreign Application Priority Data should be:  
Mar. 9, 2016 (JP) .........................2016-046037  
Apr. 3, 2015 (JP) .........................2015-076875

Signed and Sealed this  
Thirty-first Day of December, 2019

Andrei Iancu  
*Director of the United States Patent and Trademark Office*